US005667763A

United States Patent [19]

Price et al.

[11] Patent Number: 5,667,763
[45] Date of Patent: Sep. 16, 1997

[54] RADIOLABELLED AMINO ACID FORMULATIONS STORED IN AN UNFROZEN STATE

[75] Inventors: Roger Malcolm Price, Buckinghamshire; Christopher Charles May, Hertfordshire; Elizabeth Margaret Buckley; Timothy Stone, both of Buckinghamshire, all of Great Britain

[73] Assignee: Amersham International plc, Buckinghamshire, United Kingdom

[21] Appl. No.: 666,834

[22] Filed: Jun. 19, 1996

Related U.S. Application Data

[60] Division of Ser. No. 467,802, Jun. 6, 1995, which is a continuation-in-part of Ser. No. 107,733, Aug. 23, 1993, Pat. No. 5,494,654.

[30] Foreign Application Priority Data

Apr. 30, 1992 [EP] European Pat. Off. ............ 923039051

[51] Int. Cl.$^6$ ............... A61K 51/00; G01N 33/566; G01N 23/00; C09K 11/04
[52] U.S. Cl. .............. 424/1.11; 424/1.81; 436/501; 436/57; 252/625
[58] Field of Search ................ 424/1.81, 1.11; 436/501, 57; 252/625

[56] References Cited

U.S. PATENT DOCUMENTS

| | | | |
|---|---|---|---|
| 4,390,517 | 6/1983 | O'Brien et al. ................ | 424/1 |
| 4,411,811 | 10/1983 | Tzodikov ...................... | 424/1.1 |
| 4,793,987 | 12/1988 | Henderson et al. ........... | 424/1.1 |

OTHER PUBLICATIONS

1991 Amersham Life Science Products Catalog, p. 2.111. 1991.
1992 Amersham Life Science Products Catalog, pp. 54–59. 1992.
1976 New England Nuclear Catalog, p. 121 (1976).
Instruction Manual for Rianen Assay System, Prostatic Acid Phosphatase [$^{125}$I] Radioimmunoassay Kit, Catalog No. NEA–080, DuPont Medical Products Department (publication date not clear).
G.E. Abraham, *Acta Endocrinologica*, 75, Suppl. 183, 1–42 (1977).
G.E. Abraham et al., *Handbook of Radioimmunoassay*, G.E. Abraham, ed., 634, 635, 653 (1977).
A.C. Peacock et al., *Biochemistry*, 6, 1818–1827 (1967).
U.K. Laemmli, *Nature*, 227, 680, 681, 685 (1970).
A.M. Maxam et al., *Proc. Natl. Acad. Sci. USA*, 74, 500–560 (1977).
F. Sanger et al., *J. Mol. Biol.*, 94, 441–448 (1975).
D. Ornstein et al., *BioTechniques*, 3, 476–480, 482, 483 (1985).
E.A. Evans, *Radiotracer Techniques and Applications*, vol. 1, E.A. Evans and M. Muramatsu, eds., Marcel Dekker, New York, 237–260 (1977).

*Primary Examiner*—John Kight
*Assistant Examiner*—Lara C. Kelley
*Attorney, Agent, or Firm*—Wenderoth, Lind & Ponack

[57] ABSTRACT

Additives are proposed for compositions comprising radiolabelled organic compounds e.g. 32P-labelled nucleotides. Stabilizers are selected from tryptophan, para-aminobenzoate, indoleacetate and the azole group. Dyes are selected from Sulphorhodamine B, Xylene Cyanol, Azocarmine B and New Coccine. Preferred compositions contain both stabilizer and dye.

6 Claims, No Drawings

RADIOLABELLED AMINO ACID FORMULATIONS STORED IN AN UNFROZEN STATE

This is a divisional application of Ser. No. 08/467,802, filed Jun. 6, 1995; now allowed which is a continuation-in-part of Ser. No. 08/107,733, filed Aug. 23, 1993; now U.S. Pat. No. 5,494,654 which is a 371 of PCT/GB93/00869, filed Apr. 27, 1993.

Radiolytic self-decomposition of radiochemicals has always been a problem to manufacturers and users alike. Shelf-life can be as little as a few weeks despite the use of the most suitable storage temperatures and physical dispersal methods for each particular compound or isotope. The subject is discussed in Review 16, Self-decomposition of Radiochemicals, Amersham International plc, Amersham.

Generally applicable additives which could be added to radiochemicals in order to extend shelf-life and improve efficiency by minimising the formation of radioactive impurities, would be of great economic and scientific value. A user of a stabilised radiochemical would benefit from being able to conduct experiments over a longer time span, achieve more consistent results between batches of the same radiochemical, and use less rigorous storage conditions. The additive should minimally interfere with or be compatible with the processes occurring in the application of radiochemicals to experimental systems, such as protein or nucleic acid manipulation.

U.S. Pat. No. 4,390,517 teaches the use of a wide range of soluble primary, secondary and tertiary amines as stabilisers for radiolabelled compounds.

U.S. Pat. No. 4,411,881 teaches the use of thiocarbonylated amines as stabilisers.

U.S. Pat. No. 4,451,451 teaches the use of 4-aminobenzoic acid as an antioxidant in compositions containing Technetium-99m.

U.S. Pat. No. 4,793,987 teaches the use of a range of pyridine carboxylic acids as stabilisers.

32-P radiolabelled nucleotides are often sold as buffered aqueous solutions shipped in dry ice and sold for storage by the customer at $-20°$ C. It would be a significant advantage, both to the shipper and to the customer, if the radiolabelled nucleotides could be supplied at ambient temperature and stored in an unfrozen form.

Solutions of radiolabelled nucleotides and other organic compounds are generally sold colourless. A coloured solution would be an advantage, since it would make the solution more easily visible during manipulation. However, a suitable dye would need not to interfere with any process in which the radiolabelled organic chemical might be used.

In one aspect the invention provides a composition comprising an organic compound labelled with a β-emitting radionuclide, said radiolabelled organic compound being subject to radiolytic decomposition during storage and shipment, together with a stabiliser selected from tryptophan, para-aminobenzoate, indoleacetate, luminol, and the group of azoles which are compounds having a 5-membered ring with at least two ring nitrogen atoms directly bonded to one another.

In another aspect, the invention provides a composition comprising a solution of an organic compound labelled with a β-emitting radionuclide and a dye.

The invention is mainly concerned with radiolabelled organic compounds which are supplied, shipped and stored in solution, usually aqueous solution or less usually in solution in a hydrophilic organic solvent. The invention also encompasses compositions in the solid state e.g. those produced by lyophilising or otherwise drying liquid compositions. The invention is applicable to radiolabelled organic compounds which are subject to radiolytic self-decomposition, for example: amino acids, steroids, lipids, fatty acids, peptides, carbohydrates, proteins, and particularly nucleotides, thionucleotides, nucleosides and nucleic acids.

The nature of the β-emitting radionuclide is not critical; 3-H and 14-C are possible, but 32-P, 35-S and 33-P are preferred.

The stabiliser is preferably selected from L-and D-tryptophan; para-aminobenzoate which term is used to include the free acid and salts and esters thereof; indoleacetate which term is used to include the free acid and salts and esters thereof; luminol (3-aminophthalhydrazide); and the group of azoles which are compounds having a 5-membered ring with at least two ring nitrogen atoms directly bonded to one another. Such compounds preferably have the structure

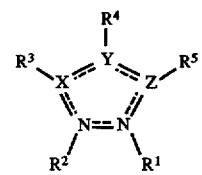

which structure contains two ring double bonds, wherein
one or two of X, Y and Z may represent N or one of X, Y and Z may represent S, the remaining X, Y and Z representing C,
when present each of $R^1$, $R^2$, $R^3$, $R^4$ and $R^5$, represents —OH, —SH, —H, —COOH, —NH$_2$, —CH$_3$ attached to the ring directly or via a chain of up to 10 carbon atoms, or two adjacent members of $R^1$, $R^2$, $R^3$, $R^4$ and $R^5$ may together constitute an aromatic ring.

It will be understood that $R^1$, $R^2$, $R^3$, $R^4$ and $R^5$ will or will not be present depending on the nature of X, Y and Z and on the positions of the two double bonds. Examples of classes of azole compounds envisaged are

| X | Y | Z | Present | Absent |
|---|---|---|---|---|
| C | C | C | $R^1$, $R^3$, $R^4$, $R^5$ | $R^2$ |
| N | C | C | $R^1$, $R^4$, $R^5$ | $R^2$, $R^3$ |
| N | N | C | $R^1$, $R^5$ | $R^2$, $R^3$, $R^4$ |
| C | N | C | $R^3$, $R^4$, $R^5$ | $R^1$, $R^2$ |
| C | N | C | $R^1$, $R^3$, $R^5$ | $R^2$, $R^4$ |
| C | S | C | $R^3$, $R^5$ | $R^1$, $R^2$, $R^4$ |

Among the possible compounds from the azole group are those illustrated in the Examples. The concentration of stabiliser is sufficient to reduce radiolytic decomposition of the radiolabelled organic compound, while not being so high as to materially interfere with the reaction systems where the radiolabelled organic compound is to be used. Preferred concentrations in liquid compositions are in the range of 1 mM to 1M, particularly 10 to 100 mM. Used in these concentrations, the preferred compounds have proved effective stabilisers particularly for nucleotides.

The dye is preferably selected from Sulphorhodamine B, Xylene Cyanol, Azocarmine B and New Coccine. Other possible dyes include Orange G, Tartrazine, Safranin O, Methyl Green, Bromophenol Blue, Eosin, Evans Blue, Brilliant Blue G, Bromocresol Green, Ponceau S, Carmoisine Red, Remazol Red RB, Sandoz Black, Sandoz Violet, Sandoz Brilliant Green, Remazol Golden Yellow, Remazol Red B, Acid Red 40, Acid Alizarin Violet N, Mordant Brown 6 and BPBDTC (3,3'-(4,4'-biphenylene)-bis(2,5-diphenyl-2H-tetrazolium chloride). The concentration of the dye should be sufficient to visibly colour the solution, but not so high as to materially interfere with the reaction systems into which the radiolabelled organic compound is to be introduced. Preferred dye concentrations are from 20 to 3000 µg/ml, particularly 50 to 400 µg/ml; that is to say approximately (depending on the molecular weight of the dye) from $3 \times 10^{-5}$ to $6 \times 10^{-3}$ mol/l particularly $8 \times 10^{-5}$ to $1 \times 10^{-3}$ mol/l. At these concentrations, the dyes do have a mild stabilising effect, in addition to providing colour. However, the colour of compositions containing these dyes does fade with time, possibly due to radiolytic rupture of double bonds of the ring structures of the dyes. While this fading does not render the compositions unworkable, it may nevertheless be inconvenient. The structural formulae of the preferred stabilisers and dyes used in this invention are given in Tables 1 and 2 respectively.

According to a further and preferred aspect of the invention, the radiolabelled organic compound composition includes both the dye and the stabiliser. This has several advantages. The stabiliser helps to prevent the dye from fading. The dye improves the visibility of the radiochemical. The dye and the stabiliser may act synergistically to improve the stability of the radiolabelled organic compound.

The compositions of this invention may contain buffers. The nature of the buffer is not critical to the invention, but standard commercial diluents for nucleotides consisting of an aqueous buffered solution stabilised by 2-mercaptoethanol or dithiothreitol are preferred systems. These are the systems that are used in the examples below. But other systems have been tested and shown to be equally effective.

Radiolabelled nucleotides and other organic compounds are conventionally shipped and stored at −20° C. or below, requiring the use of dry ice. Preferred compositions according to this invention are suitable for shipment and storage either at 4° C. (on ice) or more preferably at ambient temperature.

Transport of radioactive materials is subject to strict international regulations, which are particularly stringent in the case of air shipment. Regulations for the Safe Transport of Radioactive Materials (1985 edition) are defined in the IAEA Safety Standards (amended 1990). These list the properties required of packaging for radioactive materials, such as type A packages containing radioactive liquids.

The IAEA Safety Standards apply to international shipment. Other regulations are applicable to transport within USA and other countries.

A complete package for shipment will generally consist of a closed vessel or vial for the radioactive material, and an outer container and external packaging eg. an expanded polystyrene box and a cardboard outer layer. The entire package must meet specified requirements and pass a variety of tests in order to be suitable for shipment under the Regulations. One such requirement for type A packages is that the containment system of the package, and thus the closed vessel or vial itself, must retain its radioactive contents under a reduction of ambient pressure to 25 kPa (0.25kgf/cm$^2$). Other requirements of the packaging can be found in the above-mentioned regulations and in other regulations as appropriate.

Thus, a closed vessel or vial for containing a composition according to the invention, said vessel or vial adapted for storage and shipment will need to meet the relevant international regulations for shipment of that particular composition. One such vial which is available commercially and which may be used for shipment of compositions according to the invention is the Amersham Redivial (trade mark). A particular feature of the Redivial is a splash guard to contain the liquid contents at the bottom of the vial thus minimising contamination of the inner surfaces of the vial and cap during ambient shipment when the material is not frozen.

EXPERIMENTAL

In the examples below, various compositions were made up and tested for stability. Some of the tabulated experimental data refers to batches of dCTP labelled with 32 Phosphorus, but the stabilising compounds were also tested with the other 32 Phosphorus alpha-labelled nucleotides dATP, dGTP and dTTP. Testing of these stabilisers was also carried out with 32 Phosphorus gamma-labelled ATP and with 35 Sulphur alpha-labelled dATP. The half-life of 32P is 14.3 days, but batches for sale are typically reference-dated for the Friday of the week following sale. Stability testing was therefore carried out for 21 days to approximate the length of customer usage. Stabilisation of various compounds labelled with 3H, 14C and 33P was also investigated.

All test results are expressed as absolute percentage incorporation of the nucleotide compared with a control formulation, from the same batch, based on the above diluent without further added stabiliser or dye and stored at RT or +4° C. or −20° C.

Various tests of nucleotide stability were performed:

The radiochemical purity of the labelled nucleotide was measured after storage for various intervals, using thin layer chromatography plates which were subsequently scanned using a Raytek RITA scanner. This is reported as RCP.

Formulations were tested in various nucleic acid assays and manipulations: Sanger dideoxy sequencing using T7, Taq and Klenow DNA polymerase enzymes, random primed and nick translated DNA labelling reactions on both phage lambda and human genomic probes such as raf-1 and N-ras, and PCR labelling of probes. Probes generated as above were used in genomic hybridisations for single copy detection, and in colony screening. 3' end tailing and 5' end labelling of probes were also carried out, the latter specifically using the 32 Phosphorus gamma-labelled ATP.

Other techniques used were cDNA first strand synthesis and protein phosphorylation.

From these, random primed probe generation (in Amersham International Multiprime kit reactions: Amersham kit RPN 1600 based on Feinberg and Vogelstein, Anal. Biochem. 132, 6–13 (1983) and Addendum Anal. Biochem. 137, 266–267 (1984)) was selected as providing a stringent and representative test of radiolabelled organic compound stability and activity for the dNTPs: 5' end labelling was selected as the principal test for 32 P gamma-labelled ATP.

In the following examples, RCP refers to the radiochemical purity of the sample, MP to % incorporations obtained using the random primed DNA labelling technique in Amersham International's Multiprime kit.

SB, XY, AB and NC are Sulphorhodamine B, Xylene Cyanol, Azocarmine B and New Coccine respectively. pABA is para-aminobenzoate. IAA is indoleacetic acid. 2ME is 2-mercaptoethanol and DTT is dithiothreitol.

Storage conditions designated +40/RT/+4 indicate that the nucleotide was stored at +40° C. for 24 hours, then at room temperature (RT; 21°–24° C.) for 48 hours before being stored at +4° C. for the remainder of the test period.

Control samples consist of Amersham International's current selling nucleotide formulation, without the addition of any further stabiliser or dye.

EXAMPLES 1 TO 8

In Examples 1–8, the 32P labelled nucleotide (dCTP) was used at a specific activity of 3000 Ci/mmol and a concentration of 10 mCi/ml. 1 mCi lots were used for tests. Unless otherwise stated, the formulation used was an aqueous buffered diluent stabilised by 2-mercaptoethanol.

Example 1

Formulations containing different concentrations of stabilisers were tested. All stabilisers worked well.

| SAMPLE | STORAGE | DAY 8 | | DAY 15 | | DAY 22 | |
|---|---|---|---|---|---|---|---|
|  |  | RCP | MP | RCP | MP | RCP | MP |
| CONTROL | +40/RT/+4 | — | 1 | 21 | — | 12 | 0 |
| L-TRYPTO-PHAN 25 mM | " | 70 | 54 | 78 | — | 69 | 60 |
| pABA Na 50 mM | " | 79 | 73 | 77 | — | 79 | 66 |
| pABA K 50 mM | " | 80 | 71 | 82 | — | 79 | 70 |
| IAA 50 mM | " | 81 | 74 | 83 | — | 77 | 64 |

Example 2

Formulations containing the two dyes Sulphorhodamine B and Xylene Cyanol were made up and tested under different temperature storage conditions. Both dyes are seen to have a minor stabilising effect at +4° C.

| SAMPLE | STORAGE | DAY 7 | | DAY 14 | | DAY 23 | |
|---|---|---|---|---|---|---|---|
|  |  | RCP | MP | RCP | MP | RCP | MP |
| CONTROL | −20° C. | 87 | 68 | 79 | 65 | 82 | 67 |
| SB 400 µg/ml | " | 87 | 61 | 81 | 65 | 84 | 69 |
| XY 400 µg/ml | " | 77 | 60 | 73 | 64 | 74 | 60 |
| CONTROL | +40/RT/+4 | 13 | 11 | 6 | 0 | 0 | 0 |
| SB 400 µg/ml | " | 35 | 35 | 15 | 9 | 0 | 0 |
| XY 400 µg/ml | " | 29 | 30 | 16 | 5 | 0 | 0 |

Example 3

Formulations containing the stabiliser pABA K at the normal concentration of 50 mM and the dye New Coccine were tested. The dye was used at a final molarity of $3.5 \times 10^{-4}$ mol/l (equivalent to Sulphorhodamine B at 200 µg/ml). Storage was at RT, 37° C. or 42°–45° C. for either 1, 2 or 3 days as indicated, to test the robustness of the dye. After this period, all pots were stored at +4° C. for the remainder of the test period.

| SAMPLE | STORAGE | WK 0 | | WK 1 | | WK 2 | | WK 3 | |
|---|---|---|---|---|---|---|---|---|---|
|  |  | RCP | MP | RCP | MP | RCP | MP | RCP | MP |
| CONTROL | −20° C. | 95 | 88 | 91 | 82 | 91 | 91 | — | 73 |
| CONTROL | +40/RT/+4 | 89 | 80 | 94 | 57 | 95 | 66 | — | 12 |
| NC + pABA K | 72 HRS @ RT | 92 | 75 | 93 | 71 | 76 | 76 | — | — |
| NC + pABA K | 24 HRS @ 37 | 97 | 72 | 91 | 82 | 82 | 83 | — | 74 |
| NC + pABA K | 48 HRS @ 37 | 92 | 64 | 92 | 83 | 91 | 82 | — | 64 |
| NC + pABA K | 72 HRS @ 37 | 79 | 73 | 94 | 83 | 94 | 79 | — | — |
| NC + pABA K | 24 HRS @ 42 | 89 | 75 | 94 | 81 | 90 | 79 | — | 36 |
| NC + pABA K | 48 HRS @ 42 | 92 | 81 | 93 | 76 | 91 | 69 | — | — |
| NC + pABA K | 72 HRS @ 42 | 96 | 77 | 77 | 81 | 91 | 76 | — | — |

Example 4

RCP's and % incorporations using the Multiprime assay were also measured for Azocarmine B, with experimental details as for Example 3. The dye was used at a final molarity of $3.5 \times 10^{-4}$ mol/l

| SAMPLE | STORAGE | WK 0 RCP | WK 0 MP | WK 1 RCP | WK 1 MP | WK 2 RCP | WK 2 MP | WK 3 RCP | WK 3 MP |
|---|---|---|---|---|---|---|---|---|---|
| CONTROL | −20° C. | 93 | 89 | 88 | 82 | 93 | 91 | — | 71 |
| CONTROL | +40/RT/+4 | 93 | 88 | 64 | 58 | 73 | 39 | — | 4 |
| AB + pABA K | 72 HRS @ RT | 91 | 79 | 89 | 86 | 81 | 74 | — | — |
| AB + pABA K | 24 HRS @ 37 | 91 | 88 | 93 | 83 | 89 | 81 | — | 76 |
| AB + pABA K | 48 HRS @ 37 | 93 | 77 | 92 | 80 | 91 | 77 | — | 66 |
| AB + pABA K | 72 HRS @ 37 | 93 | 81 | 92 | 73 | 93 | 69 | — | — |
| AB + pABA K | 24 HRS @ 42 | 94 | 73 | 93 | 76 | 91 | 71 | — | 78 |
| AB + pABA K | 48 HRS @ 42 | 90 | 82 | 93 | 81 | 93 | 78 | — | — |
| AB + pABA K | 72 HRS @ 42 | 93 | 50 | 92 | 77 | 91 | 68 | — | — |

Example 5

Formulations containing two different dyes and two different stabilisers were tested. Both dyes were used at a concentration of 400 µg/ml. L-Tryptophan and potassium p-aminobenzoate were used at concentrations of 25 mM and 50 mM respectively.

| SAMPLE | STORAGE | DAY 8 RCP | DAY 8 MP | DAY 15 RCP | DAY 15 MP | DAY 21 RCP | DAY 21 MP |
|---|---|---|---|---|---|---|---|
| CONTROL | +40/RT/+4 | 12 | 2 | 6 | 1 | 3 | 1 |
| SB 400 µg/ml + L Tryp | +40/RT/+4 | 71 | 48 | 66 | 49 | 61 | 34 |
| SB 400 µg/ml + pABA K | +40/RT/+4 | 76 | 52 | 67 | 53 | 66 | 41 |
| XY 400 µg/ml + L Tryp | +40/RT/+4 | 75 | 67 | 62 | 58 | 55 | 40 |
| XY 400 µg/ml + pABA K | +40/RT/+4 | 79 | 66 | 71 | 67 | 70 | 61 |

Example 6

A formulation containing 50 mM pABA $K^+$ was stored at RT, 37° C. or 42°–45° C. for either 1, 2 or 3 days to test the robustness of the stabiliser.

All conditions except the control contain 50 mM pABA K.

After times at elevated temperatures as indicated, all conditions were stored at +4° C. for the remaining test period except for the unstabilised control, which was kept at −20° C. throughout.

| SAMPLE | STORAGE | DAY 7 RCP | DAY 7 MP | DAY 14 RCP | DAY 14 MP |
|---|---|---|---|---|---|
| CONTROL | −20° C. | 89 | 85 | 86 | 78 |
| pABA K | 24 HRS @ RT | 86 | 73 | 84 | 75 |
| " | 48 HRS @ RT | 86 | 71 | 83 | 74 |
| " | 72 HRS @ RT | 85 | 74 | 83 | 72 |
| " | 24 HRS @ 37 | 87 | 71 | 83 | 74 |
| " | 48 HRS @ 37 | 88 | 69 | 83 | 73 |
| " | 72 HRS @ 37 | 86 | 83 | 83 | 73 |
| " | 24 HRS @ 42 | 86 | 71 | 83 | 72 |
| " | 48 HRS @ 42 | 86 | 79 | 84 | 72 |
| " | 72 HRS @ 42 | 87 | 70 | 83 | 72 |

Example 7

Formulations containing different concentrations of Sulphorhodamine B as dye and para-amino Benzoic acid (Potassium salt) as stabiliser, and combinations of the two in various concentrations, were tested.

| SAMPLE | STORAGE | DAY 7 RCP | DAY 7 MP | DAY 15 RCP | DAY 15 MP | DAY 22 RCP | DAY 22 MP |
|---|---|---|---|---|---|---|---|
| CONTROL | −20° C. | 84 | 74 | 67 | 67 | 75 | 63 |
| 20 mM pABA K | +40/RT/+4 | 83 | 68 | 71 | 59 | 68 | 49 |
| 30 mM pABA K | +40/RT/+4 | 84 | 65 | 79 | 63 | 74 | 53 |
| 40 mM pABA K | +40/RT/+4 | 86 | 67 | 84 | 64 | 78 | 54 |
| 50 mM pABA K | +40/RT/+4 | 89 | 69 | 86 | 70 | 81 | 62 |
| 50 µg/ml SB | +40/RT/+4 | 20 | 8 | 7 | 1 | 0 | 0 |
| 100 µg/ml SB | +40/RT/+4 | 23 | 10 | 6 | 1 | 0 | 0 |
| 200 µg/ml SB | +40/RT/+4 | 30 | 18 | 10 | 4 | — | 0 |
| 400 µg/ml SB | +40/RT/+4 | 37 | 24 | 16 | 8 | 20 | 0 |
| 20 mM pABAK//50 µg/ml SB | +40/RT/+4 | 73 | 60 | 68 | 57 | 66 | 51 |
| 20 mM pABAK//100 µg/ml SB | +40/RT/+4 | 74 | 62 | 71 | 57 | 66 | 52 |
| 20 mM pABAK//200 µg/ml SB | +40/RT/+4 | 73 | 56 | 69 | 51 | 62 | 51 |
| 20 mM pABAK//400 µg/ml SB | +40/RT/+4 | 78 | 65 | 77 | 54 | 67 | 54 |
| 30 mM pABAK//50 µg/ml SB | +40/RT/+4 | 85 | 68 | 75 | 64 | 72 | 56 |
| 30 mM pABAK//100 µg/ml SB | +40/RT/+4 | 83 | 70 | 77 | 83 | 71 | 68 |
| 30 mM pABAK//200 µg/ml SB | +40/RT/+4 | 77 | 66 | 71 | 75 | 70 | 57 |
| 30 mM pABAK//400 µg/ml SB | +40/RT/+4 | 80 | 67 | 76 | 67 | 75 | 59 |
| 40 mM pABAK//50 µg/ml SB | +40/RT/+4 | 79 | 68 | 78 | 63 | 79 | 60 |
| 40 mM pABAK//100 µg/ml SB | +40/RT/+4 | 84 | 65 | 78 | 62 | 77 | 58 |
| 40 mM pABAK//200 µg/ml SB | +40/RT/+4 | 86 | 67 | 78 | 63 | 77 | 59 |
| 40 mM pABAK//400 µg/ml SB | +40/RT/+4 | 86 | 67 | 84 | 65 | 79 | 63 |
| 50 mM pABAK//50 µg/ml SB | +40/RT/+4 | 88 | 71 | 87 | 63 | 83 | 63 |
| 50 mM pABAK//100 µg/ml SB | +40/RT/+4 | 88 | 69 | 85 | 64 | 81 | 66 |
| 50 mM pABAK//200 µg/ml SB | +40/RT/+4 | 86 | 72 | 87 | 63 | 81 | 66 |
| 50 mM pABAK//400 µg/ml SB | +40/RT/+4 | 87 | 75 | 86 | 65 | 81 | 67 |

Example 8

Formulations containing different stabilisers were made up with and without 400 µg/ml of Sulphorhodamine B. were temperature cycled at +40° C. for 24 hours and room temperature for 48 hours before long term storage at +4° C. All samples contained 20 mM Dithiothreitol (DTT).

| SAMPLE | STORAGE | DAY 8 RCP | DAY 8 MP | DAY 15 RCP | DAY 15 MP | DAY 22 RCP | DAY 22 MP |
|---|---|---|---|---|---|---|---|
| CONTROL | +40/RT/+4 | — | 1 | 21 | — | 12 | 0 |
| SB 400 µg/ml//50 mM LTRYP | +40/RT/+4 | 70 | 45 | 82 | — | 73 | 63 |
| SB 400 µg/ml//50 mM pABANa | +40/RT/+4 | 79 | 72 | 88 | — | 78 | 72 |
| SB 400 µg/ml//50 mM pABAK | +40/RT/+4 | 83 | 73 | 88 | — | 80 | 72 |
| L TRYPTOPHAN ONLY | +40/RT/+4 | 70 | 54 | 78 | — | 69 | 60 |
| pABA Na ONLY | +40/RT/+4 | 79 | 73 | 77 | — | 79 | 66 |
| pABA K ONLY | +40/RT/+4 | 80 | 71 | 82 | — | 79 | 70 |

Example 9

In the following data, the nucleotide used in testing was $^{35}$S dATP at a concentration of 10 mCi/ml. All the stabilising compounds were used at a concentration of 50 mM, and

| SAMPLE | WK 2 RCP | WK 2 MP | WK 4 RCP | WK 4 MP | WK 8 RCP | WK 8 MP | WK 14 RCP | WK 14 MP |
|---|---|---|---|---|---|---|---|---|
| CONTROL −20° C. | 92 | 72 | 91 | 74 | 91 | 77 | 87 | 61 |
| 3-Amino-5-mercaptotriazole | 92 | 67 | 91 | 73 | 89 | 78 | 88 | 53 |
| 2-Amino-1,3,4-thiadiazole | 87 | 72 | 84 | 74 | 81 | 74 | 75 | 61 |
| 2,5-Dimercapto-1,3,4-thiadiazole | 92 | 62 | 90 | 80 | 90 | 77 | 87 | 47 |
| 4-Methyl-4H-1,2,4-triazole-3-thiol | 91 | 66 | 88 | 79 | 91 | 72 | 83 | 43 |
| 3,5-Diamino-1,2,4-triazole | 91 | 73 | 84 | 75 | 83 | 73 | 65 | 53 |
| 3-Amino pyrazole | 88 | 73 | 87 | 70 | 85 | 78 | 71 | 53 |
| 5-Amino-1,3,4-thiadiazole-2-thiol | 92 | 79 | 92 | 79 | 94 | 88 | 71 | 70 |
| 3-Amino-5-hydroxypyrazole | 64 | 71 | 84 | 71 | 83 | 75 | 72 | 63 |
| 1H-1,2,4-triazole-3-thiol | 91 | 70 | 91 | 73 | 89 | 81 | 90 | 78 |
| 5-Mercaptotriazole | 91 | 73 | 91 | 78 | 89 | 78 | 86 | 55 |

| | WK 2 | | WK 4 | | WK 8 | | WK 14 | |
|---|---|---|---|---|---|---|---|---|
| SAMPLE | RCP | MP | RCP | MP | RCP | MP | RCP | MP |
| (Na⁺) 2H₂O | | | | | | | | |
| p-Amino benzoic acid (K⁺) | 79 | 60 | 81 | 69 | 66 | 66 | 58 | 40 |
| 5-Mercapto-1-tetrazole acetic acid (Na⁺) | 91 | 75 | 86 | 80 | 78 | 70 | 53 | 40 |
| 5-Metcapto-1-methyl tetrazole | 89 | 73 | 84 | 65 | 78 | 70 | 65 | 37 |

Stabilisation was observed in all formulations.

Example 10

The stabilisers of Example 9 were also tested on 32P dCTP labelled nucleotide where they were again used at a working concentration of 50 mM. The radioactive concentration of the dCTP was 10 mCi/ml. All samples contained 5 mM 2-mercaptoethanol. Storage conditions were +40/RT/+4 except for the −20° C. control.

shows the stabiliser and/or dye present in each sample including their respective concentrations. Storage conditions were +40/RT/+4 except for the −20° C. control.

| | DAY 6 | | DAY 14 | | DAY 21 | |
|---|---|---|---|---|---|---|
| SAMPLE | RCP | MP | RCP | MP | RCP | MP |
| CONTROL −20° C. | 79 | 71 | 80 | 68 | 79 | 70 |
| 3-Amino-5-mercaptotriazole | 77 | 70 | 76 | 68 | 76 | 66 |
| pABA K⁺ | 78 | 65 | 76 | 63 | 71 | 61 |
| 2-Amino-1,3,4-thiadiazole | 73 | 60 | 65 | 58 | 68 | 51 |
| 2,5-Dimercapto-1,3,4-thiadiazole | 79 | 74 | 78 | 67 | 79 | 65 |
| 4-Methyl-4H-1,2,4-triazole-3-thiol | 78 | 75 | 78 | 77 | 79 | 69 |
| 3,5-Diamino-1,2,4-triazole | 78 | 72 | 76 | 73 | 74 | 65 |
| 5-Mercapto-1-tetrazole acetic acid (Na⁺) | 81 | 69 | 73 | 68 | 73 | 65 |
| 5-Mercapto-1-methyl tetrazole | 75 | 70 | 77 | 66 | 71 | 70 |
| 3-Amino pyrazole | 76 | 73 | 76 | 65 | 74 | 63 |
| 5-Amino-1,3,4-thiadiazole-2-thiol | 72 | 83 | 78 | 70 | 74 | 66 |
| 3-Amino-5-hydroxypyrazole | 69 | 76 | 74 | 64 | 68 | 58 |
| 1H-1,2,4-triazole-3-thiol | 76 | 72 | 78 | 72 | 78 | 64 |
| 5-Mercaptotriazole (Na⁺) 2H₂O | 75 | 71 | 78 | 68 | 76 | 67 |

The results indicate that these compounds showed stabilising activity of nucleotides in solution.

Example 11

Further compounds were also tested on the 32P labelled dCTP nucleotides as for Example 10, and were again used at a working concentration of 50 mM (except for luminol which was used at a working concentration of 45 mM).

| | DAY 8 | | DAY 16 | | DAY 23 | |
|---|---|---|---|---|---|---|
| SAMPLE | RCP | MP | RCP | MP | RCP | MP |
| CONTROL −20° C. | 90 | 50 | 88 | 52 | 83 | 49 |
| pABA K⁺ | 87 | 44 | 82 | 33 | 78 | 31 |
| 5-Methyl-1H-benzotriazole | 80 | 40 | 71 | 39 | 67 | 48 |
| 3-Amino-4-pyrazole carboxylic acid | 84 | 45 | 81 | 42 | 75 | 47 |
| 3-Amino-5-mercaptotriazole | 87 | 41 | 88 | 40 | 82 | 47 |
| Luminol | 80 | 39 | 80 | 44 | 77 | 47 |

Example 12

Formulations containing stabiliser and/or dye were tested on dATP (alpha-35S) nucleotide solutions which were at 10 mCi/ml radioactive concentration. The labelling on the table

| SAMPLE | WK 2 RCP | WK 2 MP | WK 4 RCP | WK 4 MP | WK 8 RCP | WK 8 MP | WK 14 RCP | WK 14 MP |
|---|---|---|---|---|---|---|---|---|
| CONTROL −20° C. | 82 | 64 | 65 | 41 | 22 | 23 | 15 | 16 |
| CONTROL +40/RT/+4 | 56 | 45 | 0 | 0 | 0 | 0 | 0 | 0 |
| 20 mM DTT | 92 | 71 | 91 | 52 | 78 | 43 | 65 | 50 |
| 50 mM pABA (Na$^+$) | 88 | 77 | 77 | 43 | 76 | 44 | 54 | 45 |
| 25 mM Tryptophan | 86 | 70 | 78 | 50 | 59 | 34 | 41 | 38 |
| 200 µg/ml SB | 64 | 56 | 17 | 7 | 0 | 0 | 0 | 0 |
| 50 mM pABA, 200 µg/ml SB | 86 | 69 | 74 | 31 | 67 | 34 | 48 | 42 |
| DTT, pABA, SB 20 mM, 50 mM, 200 µg/ml | 91 | 67 | 88 | 37 | 86 | 49 | 79 | 49 |

These results show that DTT, pABA, Tryptophan and to a small extent SB, all stabilised the 35S labelled nucleotide. The possibility of dye and stabiliser combinations was demonstrated.

Example 13

Formulations containing stabilisers were tested on dATP (alpha-35S). All samples were pH 10.0. Radioactive concentration was 10 mCi/ml. The stabilisers present are indicated in the results table for each sample. Storage conditions were +40/RT/+4. AMT=3-Amino-5-mercaptotriazole.

EXAMPLES 14 TO 21

Examples 14 to 21 show further testing of stabilisers on various radiolabelled compounds. Unless otherwise indicated, all stabilisers were used at a working concentration of 50 mM.

Example 14

Stabilisers were tested on dATP (alpha 35S) nucleotide solutions. All the samples were pH 10.0 and the radioactive concentration was 10 mCi/ml. All samples contained 20 mM DTT. Storage conditions were 40/RT/+4, except for the first two controls which were stored at −20° C.

| SAMPLE | WK 2 RCP | WK 2 MP | WK 4 RCP | WK 4 MP | WK 8 RCP | WK 8 MP | WK 14 RCP | WK 14 MP |
|---|---|---|---|---|---|---|---|---|
| 20 mM DTT CONTROL −20° C. | 94 | 55 | 89 | 70 | 81 | 66 | 78 | 67 |
| 50 mM AMT | 95 | 68 | 94 | 76 | 90 | 60 | 88 | 84 |
| 50 mM AMT, 50 mM DTT | 93 | 52 | 94 | 73 | 92 | 62 | 91 | 83 |
| 50 mM AMT, 20 mM DTT | 93 | 64 | 94 | 84 | 92 | 70 | 91 | 84 |
| 50 mM AMT, 100 mM 2ME | 95 | 60 | 94 | 78 | 92 | 72 | 93 | 80 |
| 50 mM AMT, 40 mM 2ME | 94 | 50 | 93 | 73 | 92 | 70 | 90 | 77 |
| 25 mM AMT | 93 | 67 | 92 | 81 | 87 | 70 | 80 | 69 |
| 25 mM AMT, 50 mM DTT | 96 | 44 | 94 | 78 | 92 | 68 | 90 | 77 |
| 25 mM AMT, 20 mM DTT | 96 | 53 | 93 | 85 | 90 | 75 | 89 | 75 |
| 25 mM AMT, 100 mM 2ME | 95 | 45 | 94 | 72 | 92 | 76 | 92 | 83 |
| 25 mM AMT, 40 mM 2ME | 95 | 50 | 92 | 87 | 91 | 77 | 89 | 80 |

It can be deduced that the three stabilisers azole, DTT and 2-ME may be used in combination to achieve adequate stabilisation. Azole stabiliser may also be used with no other stabiliser present.

| SAMPLE | WK 2 RCP | WK 2 MP | WK 4 RCP | WK 4 MP | WK 8 RCP | WK 8 MP | WK 14 RCP | WK 14 MP |
|---|---|---|---|---|---|---|---|---|
| CONTROL −20° C. | 95 | 61 | 92 | 76 | 90 | 82 | 90 | 76 |
| CONTROL −20° C. | 93 | 51 | 91 | 78 | 87 | 80 | 87 | 76 |
| CONTROL +40/RT/+4 | 92 | 53 | 58 | 56 | 40 | 39 | 30 | 38 |
| 5-Amino-1,3,4-thiadiazole-2-thiol | 95 | 55 | 91 | 72 | 90 | 71 | 85 | 76 |
| 2-Amino-1,3,4-thiadiazole | 92 | 56 | 88 | 71 | 85 | 71 | 85 | 72 |
| 4-Methyl-4H-1,2,4-triazole-3-thiol | 91 | 49 | 88 | 63 | 87 | 64 | 91 | 68 |
| 3-Amino pyrazole | 93 | 56 | 85 | 70 | 85 | 71 | 88 | 79 |
| 3,5-Diamino triazole | 91 | 53 | 79 | 69 | 85 | 73 | 85 | 79 |

Example 15

A further experiment was carried out to test stabilisers on dATP (Alpha 35S). Experimental details were as for Example 14.

| SAMPLE | WK 2 RCP | WK 2 MP | WK 4 RCP | WK 4 MP | WK 8 RCP | WK 8 MP | WK 14 RCP | WK 14 MP |
|---|---|---|---|---|---|---|---|---|
| CONTROL −20° C. | 93 | 67 | 90 | 74 | 88 | 72 | 89 | 76 |
| CONTROL −20° C. | 93 | 65 | 90 | 76 | 87 | 77 | 84 | 74 |
| CONTROL +40/RT/+4 | 90 | 61 | 83 | 77 | 75 | 71 | 62 | 60 |
| 5-Amino-1,3,4-thiadiazole-2-thiol | 93 | 54 | 90 | 79 | 87 | 66 | 90 | 76 |
| 4-Methyl-4H-1,2,4-triazole-3-thiol | 93 | 48 | 91 | 73 | 88 | 61 | 88 | 74 |
| 3-Amino pyrazole | 91 | 64 | 87 | 78 | 83 | 70 | 80 | 80 |
| 3-Amino pyrazole-4-carboxylic acid | 91 | 61 | 86 | 82 | 83 | 72 | 79 | 80 |
| 3,5-Diamino triazole | 90 | 58 | 90 | 77 | 84 | 77 | 82 | 75 |
| 25 mM Tryptophan | 90 | 51 | 90 | 74 | — | 70 | 79 | 74 |
| 3-Amino-5-mercapto triazole | 92 | 55 | 91 | 73 | 85 | 74 | 88 | 73 |

Example 16

Stabilisers were tested on 33P gamma-labelled ATP. All samples contained 0.1% 2-mercaptoethanol. The radioactive concentration was 5 mCi/ml. All samples were stored at +4° C. except the one control sample stored at −20° C., (there was no temperature cycling).

| SAMPLE | DAY 6 RCP | DAY 14 RCP | DAY 45 RCP |
|---|---|---|---|
| CONTROL −20° C. | 88 | 86 | 83 |
| CONTROL +4° C. | 76 | 64 | 50 |
| 5-Amino-1,3,4-thiadiazole-2-thiol | 90 | 89 | 87 |
| 4-Methyl-4H-1,2,4-triazole-3-thiol | 90 | 87 | 86 |
| 3-Amino-5-hydroxy-pyrazole | 89 | 81 | 78 |
| 3-Amino-5-mercapto-triazole | 88 | 77 | 75 |
| 3,5-Diamino-1,2,4-triazole | 89 | 88 | 81 |

All stabilisers showed a stabilisation effect, with all the purities being greater than those of the +4° C. Control. The presence of some of the stabilisers maintained the purity of the nucleotide solution more effectively than storage at −20° C.

Example 17

Stabilisers were tested on 35S labelled methionine. All samples contained 0.1% 2-mercaptoethanol. The radioactive concentration was 34 mCi/ml. All samples were stored at +4° C. except the first Control sample which was stored at −20° C.

| SAMPLE | DAY 7 RCP | DAY 14 RCP | DAY 25 RCP | DAY 32 RCP |
|---|---|---|---|---|
| CONTROL −20° C. | 84 | 63 | 41 | 27 |
| CONTROL +4° C. | 52 | 10 | 3 | — |
| 5-Amino-1,3,4-thiadiazole-2-thiol | 95 | 93 | 87 | 83 |
| 4-Methyl-4H-1,2,4-triazole-3-thiol | 93 | 90 | 84 | 84 |
| 3-Amino-5-hydroxy-pyrazole | 67 | 19 | 2 | — |
| 3-Amino-5-mercapto-triazole | 94 | 94 | 92 | 92 |
| 3,5-Diamino-1,2,4-triazole | 82 | 39 | 12 | 5 |

All stabilisers provided some stabilisation compared with the 4° C. control. Several of these stabilisers conferred better stability on the 35S methionine at +4° C. than storage at −20° C. without the stabilisers present.

Example 18

Stabilisers were tested on $^3$H labelled phenylalanine. The radioactive concentration was 0.5 mCi/ml. All samples were stored at room temperature except the first Control sample which was stored at +2° C.

| SAMPLE | DAY 13 RCP | DAY 23 RCP | DAY 36 RCP | DAY 41 RCP |
|---|---|---|---|---|
| CONTROL +2° C. | 82 | 74 | 74 | 68 |
| CONTROL RT | 81 | 71 | 69 | 62 |
| 5-Amino-1,3,4-thiadiazole-2-thiol | 92 | 90 | 93 | 92 |
| 3,5-Diamino-1,2,4-triazole | 91 | 87 | 87 | 86 |
| 3-Amino-5-hydroxy-pyrazole | 92 | 88 | 93 | 92 |
| Para-aminobenzoic acid | 92 | 88 | 93 | 91 |

All stabilisers provided stabilisation compared with both control samples. Excellent stability was achieved even though storage was at room temperature.

Example 19

Stabilisers were tested on (Methyl-3H) Thymidine. The radioactive concentration was 0.5 mCi/ml. All samples were stored at room temperature except the first Control sample which was stored at +2° C.

| SAMPLE | DAY 13 RCP | DAY 23 RCP | DAY 36 RCP | DAY 41 RCP |
|---|---|---|---|---|
| CONTROL +2° C. | — | 74 | 69 | 68 |
| CONTROL RT | 78 | 73 | 66 | 64 |
| 5-Amino-1,3,4-thiadiazole-2-thiol | 86 | 87 | 85 | 85 |
| 3,5-Diamino-1,2,4-triazole | 85 | 84 | 84 | 85 |
| 3-Amino-5-hydroxy-pyrazole | 86 | 83 | 85 | 86 |
| Para-aminobenzoic acid | 85 | 86 | 85 | 86 |

All stabilisers provided some stabilisation compared with both control samples. Excellent stability was achieved even though all stabilised samples were stored at room temperature.

Example 20

Stabilisers were tested on L-(U-14C) Histidine. The radioactive concentration was 100 mCi/ml. All samples were stored at room temperature except the first Control sample which was stored at +2° C.

| SAMPLE | DAY 13 RCP | DAY 23 RCP | DAY 36 RCP | DAY 41 RCP |
|---|---|---|---|---|
| CONTROL +2° C. | 99 | 99 | 98 | 99 |
| CONTROL RT | 97 | 97 | 96 | 95 |
| 5-Amino-1,3,4-thiadiazole-2-thiol | 97 | 98 | 99 | 97 |
| 3,5-Diamino-1,2,4-triazole | 98 | 97 | 98 | 98 |
| Para-aminobenzoic acid | 99 | 98 | 98 | 97 |

The stabilisers provided some stabilisation compared with the RT control sample. All samples performed well. The 14C half-life is very long (5730 years) and because of this, 14C-labelled compounds would be expected to be more stable. Long-term stability studies would be expected to show that the samples containing stabilisers have a significant stability improvement compared with controls..pa Example 21

The stability of other compounds was determined in a similar manner. L-(5-3H) Proline (at 0.5 mCi/ml) and (8-14C) ATP (at 0.75 mCi/ml) were analysed over a period of six weeks. It was found that these compounds were quite stable, even with no stabiliser present. Both compounds maintained their purities at approximately 97–98%. From these results it can be concluded that the presence of the stabilisers does not reduce the stability of L-(5-3H) Proline and (8-14C) ATP.

TABLE 1

TRYPTOPHAN

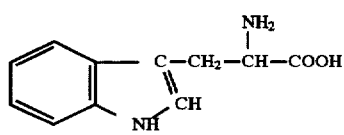

TABLE 1-continued

P-AMINOBENZOIC ACID

INDOLEACETIC ACID

5-AMINO-1,3,4-THIADIAZOLE-2-THIOL

3-AMINO-5-MERCAPTO-1,2,4-TRIAZOLE 2,4-DIMERCAPTO-1,3,4-THIADIAZOLE 3,5-DIAMINO-1,2,4-TRIAZOLE

2-AMINO-1,3,4-THIADIAZOLE

4-METHYL-4H,1,2,4-TRIAZOLE-3-THIOL

3-AMINO PYRAZOLE

TABLE 1-continued
3-AMINO-4-PYRAZOLE CARBOXYLIC ACID
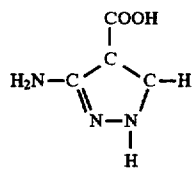
3-AMINO-5-HYDROXYPYRAZOLE
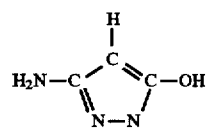
4-AMINO-1,2,4-TRIAZOLE
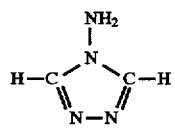
1H-1,2,4-TRIAZOLE-3-THIOL
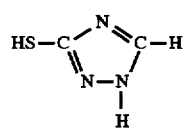
5-MERCAPTO-1,2,3-TRIAZOLE(Na$^+$ SALT)
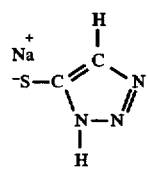
5-MERCAPTO-1-TETRAZOLEACETIC ACID (Na$^+$ SALT)
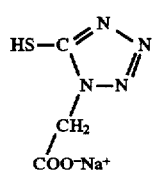
5-MERCAPTO-1-METHYL TETRAZOLE
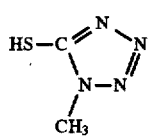
TABLE 1-continued
5-METHYL-1H-BENZOTRIAZOLE
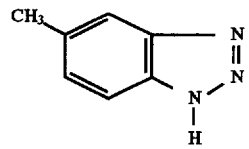
3-AMINOPHTHALHYDRAZIDE
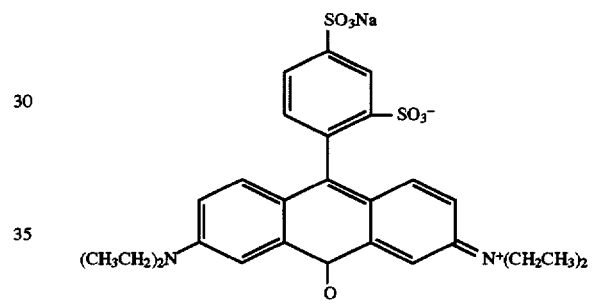
TABLE 2
SULFORHODAMINE B
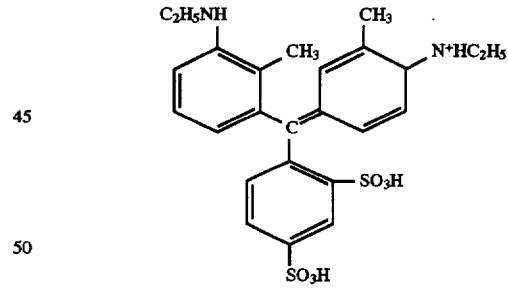
XYLENE CYANOL
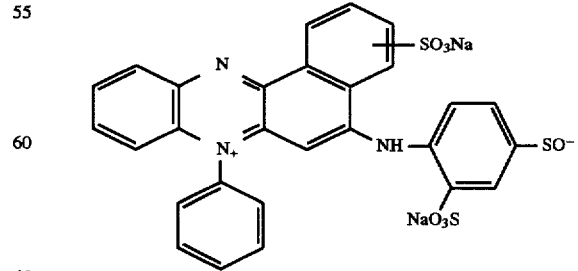
AZOCARMINE B TABLE 2-continued

NEW COCCINE

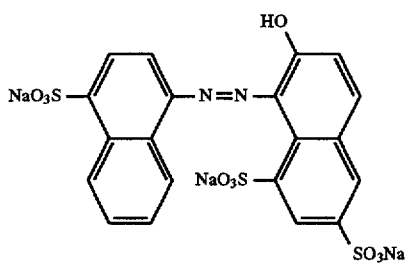

We claim:

1. A product consisting of a stabilized solution of an amino acid labelled with a β-emitting nuclide, said solution also containing a dye, and said solution contained in a unfrozen state and stable for at least seven days within a closed vessel which vessel is suitable for storage and shipment of the solution in an unfrozen state.

2. The product according to claim 1, wherein the β-emitting nuclide is $^{35}S$ or $^{3}H$ or $^{14}C$.

3. The product according to claim 1, wherein said solution consists essentially of the amino acid labelled with a β-emitting nuclide, the stabilizer and the dye, optionally together with a buffer.

4. The product according to claim 1, wherein the concentration of stabilizer in the said solution is 10 to 100 mM.

5. The product according to claim 1, wherein the dye concentration in the said solution is 50 to 400 µg/ml.

6. The product according to claim 1, wherein said solution is suitable for use in enzymatic reaction systems.

* * * * *